United States Patent [19]

Haber et al.

[11] Patent Number: 5,391,153
[45] Date of Patent: Feb. 21, 1995

[54] TROCAR WITH LINEAR MOVEMENT SEAL

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 45,857

[22] Filed: Apr. 9, 1993

[51] Int. Cl.⁶ ............................................. A61M 5/178
[52] U.S. Cl. ...................................................... 604/167
[58] Field of Search .................... 251/176, 321, 337; 604/122, 164, 166, 167, 169, 170, 171, 185, 264; 137/249

[56] References Cited

U.S. PATENT DOCUMENTS

| | | |
|---|---|---|
| 3,994,287 | 11/1976 | Turp et al. . |
| 4,177,814 | 12/1979 | Knepshield et al. . |
| 4,430,081 | 2/1984 | Timmermans .................... 604/256 |
| 4,610,665 | 9/1986 | Matsumoto et al. ................ 604/167 |
| 4,623,343 | 11/1986 | Thompson . |
| 4,654,030 | 3/1987 | Moll et al. . |
| 4,655,752 | 4/1987 | Honkanen et al. ................... 604/256 |
| 4,902,280 | 2/1990 | Lander . |
| 4,917,668 | 4/1990 | Haindl ................................ 604/167 |
| 4,931,042 | 6/1990 | Holmes et al. . |
| 5,041,095 | 8/1991 | Littrell ................................ 604/167 |
| 5,053,016 | 10/1991 | Lander . |
| 5,057,084 | 10/1991 | Ensminger et al. ................. 604/167 |
| 5,066,288 | 11/1991 | Deniega et al. . |
| 5,098,405 | 3/1992 | Peterson et al. . |
| 5,104,383 | 4/1992 | Shichman . |
| 5,127,626 | 7/1992 | Hilal et al. . |
| 5,141,498 | 8/1992 | Christian . |
| 5,167,636 | 12/1992 | Clement . |
| 5,197,955 | 3/1993 | Stephens et al. . |
| 5,226,879 | 7/1993 | Ensminger et al. .................... 604/93 |

FOREIGN PATENT DOCUMENTS

WO91/17781  11/1991  WIPO ........................... A61M 5/178

Primary Examiner—C. Fred Rosenbaum
Assistant Examiner—Perry E. Van Over
Attorney, Agent, or Firm—Townsend & Townsend Khourie & Crew

[57] ABSTRACT

A trocar (2) includes a hollow body (4) defining a path between its proximal and distal ends with an obturator assembly (6) positioned along the path. The tip (34, 36) of the obturator assembly has a cutting element (38). A novel gas sealing assembly (114) seals the path along the trocar body and includes first and second sealing elements (122) each movable laterally, typically radially, along a linear path between a sealing position, to seal the path when an object, such as an obturator barrel (14), is not positioned along the path, and an object passing position, when an object is positioned along the path. The gas sealing assembly also includes a flexible, elastic, conical element (144) with a hole (158) at its tip and raised ridges or rings (164) along its inner surface (154), for sealing the path when an object is positioned along the path.

28 Claims, 8 Drawing Sheets

TROCAR WITH LINEAR MOVEMENT SEAL

CROSS REFERENCE TO RELATED APPLICATIONS

This is related to U.S. Pat. application Ser. No. 08/015,170, filed Feb. 9, 1993 for TROCAR; U.S. Pat. application Ser. No. 08/019,548, filed Feb. 19, 1993 for TROCAR AND SEAL; U.S. Pat. application Ser. No. 08/031,174 filed Mar. 11, 1993 for TROCAR WITH OVERLAPPING SEAL ELEMENTS; U.S. Pat. application Ser. No. 08/033,315 filed Mar. 15, 1993 for TROCAR WITH IMPROVED OBTURATOR; U.S. Pat. application Ser. No. 08/039,910 filed Mar. 30, 1993 for TROCAR WITH PIVOTAL SAFETY SHIELD; and U.S. Pat. application Ser. No. 08/045,858 filed on the same date as this application for TROCAR WITH PIVOTAL SEAL, the disclosures of which are incorporated by reference.

BACKGROUND OF THE INVENTION

Practitioners of medicine or surgery frequently advise a patient to undergo an invasive procedure for either diagnostic or therapeutic reasons. One such invasive procedure involves the use of a trocar which is a sharpened cannula or cylindrical instrument for piercing the wall of a body cavity to minimize traumatization to the tissue through which the endoscopic instrument is passed and to stabilize such endoscopic instrument as well as to provide a seal for insufflation of gasses to expand the operating theater. Thus, the practitioner can gain access to the cavity to withdraw a substance such as a fluid or biopsy specimen, to introduce a gas such as carbon dioxide or an instrument, such as a surgical tool. A laparoscope, a flexible fiberoptic endoscope, is an example of a surgical instrument often introduced through a trocar. The trocar barrel also helps to avoid trauma to the tissue surrounding the opening while inserting and withdrawing a surgical instrument.

Any of the numerous body cavities can be accessible to trocar invasion. Sites for introduction of a trocar include the abdomen and the pelvis. A laparoscope can be introduced through the trocar for visualization, biopsy, and certain surgical procedures. Other body cavities which commonly benefit from endoscopic procedure include the thoracic, cranial, and various joint cavities.

A general technique for introduction of a trocar includes induction of appropriate anesthesia which may be general, local or a combination of both. The area to be pierced by the trocar, such as the skin of the abdomen, is prepped and cleansed conventionally. Typically, the operator makes a nick or a small skin incision with a scalpel blade. The sharpened tip of the conventional trocar is introduced through the nick or incision, and the conventional trocar is pushed downward to and through the fatty tissue. The conventional trocar is further pushed so that its sharpened tip pierces the muscular fascial layer to enter the abdominal cavity.

In the case of laparoscopic surgery (surgery inferior to the diaphragm) a biocompatible gas such as carbon dioxide ($CO_2$) is introduced under pressure into the abdominal cavity to create a space between the muscular fascial layer of the inner abdominal wall and the vital organs posterior to this wall. Such vital organs in the abdomen include the bowel (large and small intestine), the liver, stomach and other structures. Use of $CO_2$ insufflation of the pelvic region tends to protect the bladder and the reproductive organs as well as their associated vascular structures from inadvertent puncture by the sharpened trocar. This is so because of the increased separation between the organs resulting from the expansion of the abdominal cavity due to internal $CO_2$ gas pressure.

SUMMARY OF THE INVENTION

The present invention is directed to a seal for use with medical devices designed for minimally invasive surgical procedures. The medical device is of the type having a hollow interior defining a path which is to be fluidly sealed both when an object has and has not been directed along the path and into the hollow interior. The invention finds particular utility when used as a part of a trocar.

The seal is used for sealing the path along the body of a trocar. The seal seals the path both when the obturator or any surgical instrument is within the trocar body and once the obturator/surgical instrument has been removed from the trocar body. The seal includes an object seal designed to seal the path by engaging the outside of the obturator/surgical instrument to provide a fluid seal along the path when such objects are housed within the trocar body. One object seal is a flexible, elastic, conical valve element tapering inwardly towards the distal end of the trocar body. The seal also includes first and second sealing elements positioned along the path. The sealing elements are biased towards one another. The sealing elements have confronting sealing surfaces which sealingly engage one another when they are in the sealing position so to seal the path when an object is not positioned along the path. The sealing elements are movable laterally along a linear path from a sealing position to an object passing position.

The sealing elements preferably have elastomeric bodies with complementary elastomeric sealing surfaces which engage one another when the sealing elements are in the sealing position. The sealing elements are configured to be movable laterally from the sealing position to an object passing position by passing an object, such as an obturator or other surgical instrument, through the body. This is achieved in the preferred embodiment by making the proximally facing surfaces of the sealing elements, against which the obturator will press, tapered radially inwardly and axially distally; the axially directed force of the obturator creates a lateral force component on the sealing elements to force the sealing elements laterally outwardly against the biasing force of springs.

The hollow interior distal of the conical element is preferably selectively coupled to a pressurized gas source and to atmosphere. This allows the physician to pressurize or vent the body cavity through the trocar. It is preferred that the material for the conical element be chosen and the conical element be configured to accommodate a range of diameters from, for example, 5 mm to 11.4 mm, that is a range in diameters from x to at least 2x. Also, when configuring the object engaging surfaces and choosing the material, care must be taken to minimize the amount of force required to pass the instrument through the gas seal.

The conical sealing element is designed to accommodate an obturator assembly and virtually any conventional endoscopic surgical instrument which would be used with the trocar body after the trocar body has been mounted in place. One of the problems with known trocars is that the gas seals are designed for the obturator assembly and similarly sized endoscopic surgical instruments. However, many endoscopic surgical instruments are substantially smaller in diameter than the obturator assembly. When this occurs, the instrument can often move radially within the barrel of the conventional trocar body which can cause a loss in sealing effectiveness of the conventional gas seal. To accommodate these smaller diameter surgical instruments, conventional trocars may use smaller diameter positioning and sealing inserts mounted to the conventional trocar body at its proximal end.

The present invention has solved these problems by designing the conical sealing element within an included angle of between about 60° and 120°, preferably about 90°, and making the conical sealing element of a highly elastic, yet tough material. A suitable material has been found to be 50 Durometer silicone rubber. The hole at the tip of the conical sealing element is at most about 90% of the smallest diameter arthroscopic surgical instrument expected to be used. In the preferred embodiment the hole is about 4.6 mm in diameter. The conical sealing element is designed to accommodate obturators/surgical instruments having diameters ranging in size from at least 2 to 1 and preferably 3 to 1. In the preferred embodiment the ranges of sizes range from about 5 mm to at least 10 mm and preferably up to 15 mm.

The conical sealing element is designed to reduce axial friction on the obturator/surgical instruments which are passed through the trocar body. It has been found by placing a series of raised ridges or rings along the inner surface of the conical sealing element, the axial friction generated between the surgical instrument and the conical sealing element can be substantially reduced, thus increasing operational sensitivity for the physician.

Object seals other than the conical sealing element can be used to engage obturators and other objects passed through the trocar body. For example, a flat, highly elastic seal having a hole in the center and a number of concentric thickened areas or rings formed on at least one of the axially facing surfaces of the seal could be used. Also, a thick, soft O-ring having an oval or rectangular, instead of a round, cross-sectional shape could be used. Further, a block of self-healing silicone gel, such as made by Dow Corning of Michigan as Q7-2218, could be used; with the silicone gel, a small central hole is preferred but is not necessarily required. The main features the object seal preferably possesses include the ability to accommodate, typically by stretching, a range of diameters, the ability to exhibit low frictional qualities during both insertion and extraction of the object, and the ability to accommodate some radial movement of the object.

Other features and advantages of the invention will appear from the following description in which the preferred embodiment has been set forth in detail in conjunction with the accompanying drawings.

DESCRIPTION OF THE PREFERRED EMBODIMENT

Figure 1:
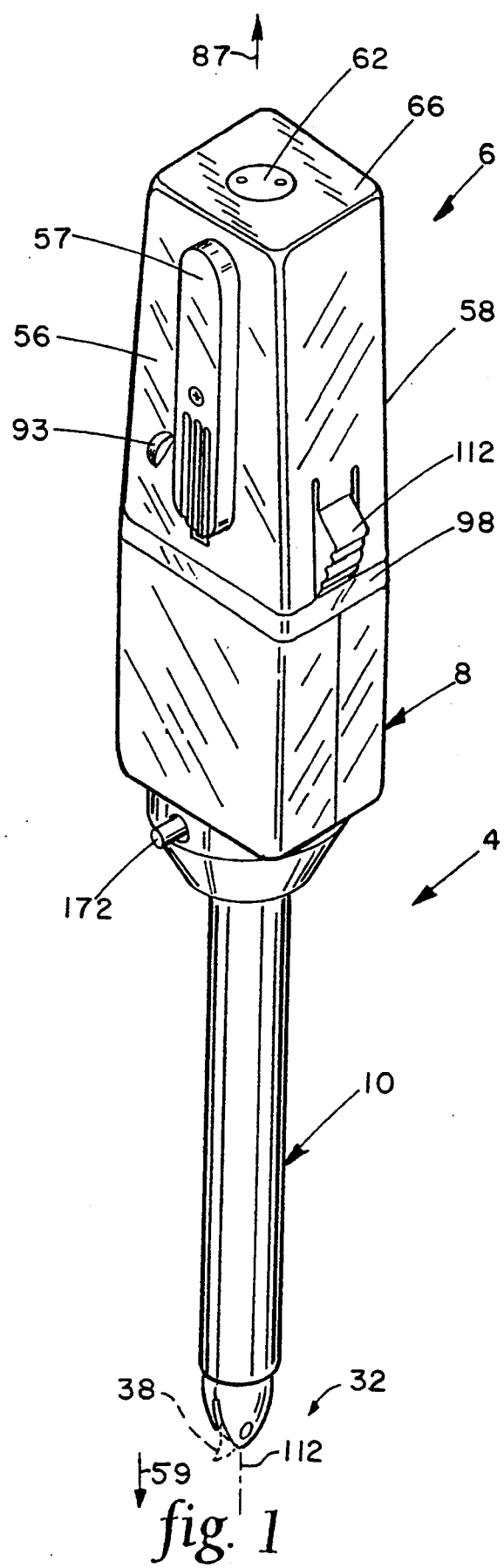
FIG. 1 is an overall isometric view of a trocar made according to the invention.

FIGS. 1–3B illustrate a trocar 2 including a trocar body 4 to and within which an obturator assembly 6 is slidably mounted. Trocar body 4 is hollow and includes a two-part trocar base 8 from which a tubular trocar barrel 10 extends. Trocar barrel 10 is secured between halves 8a, 8b of trocar base 8, such as with an adhesive. Trocar barrel 10 defines a central axis 12 of trocar 2 and is sized to guide the obturator barrel 14 therein.

Obturator assembly 6 includes an obturator barrel 14 having a flanged proximal end 16 and a distal end 18. An idler pulley support 20 is mounted to proximal end 16 using a pin 22 which passes through openings 24 formed in barrel 14 at proximal end 16 and bores 26 in legs 28 of idler pulley support 20. Pin 22 also supports an idler pulley 30 between legs 28 of idler pulley support 20. A cutting tip assembly 32 is mounted to distal end 18 of obturator barrel 14. Assembly 32 includes a pair of obturator tip shells 34, 36 and a blade 38 rotatably mounted on an axle 40 extending between tip shells 34, 36. Blade 38 has a spirally grooved outer surface 42 to accommodate one or more windings of a continuous loop cable 43. Cable 43 is thus stretched between surface 42 of blade 38 and idler pulley 30 and is housed totally within obturator barrel 14.

Upper and lower limit flanges 44, 46 are secured to obturator barrel 14 at fixed positions, such as using an adhesive. Flanges 44, 46 have radially extending tabs 48, 49 and 50 which are housed within slots 52, 54 formed in the sidewall 56 of an obturator body 58. Tab 49 is longer than tabs 48 or 50 and extends through sidewall 56. Tab 49 engages a slot 55 formed in a pivotal safety arm 57, see FIG. 2A, when arm 57 is in the position of FIG. 1 to prevent tab 49 and flange 44 therewith from moving in proximal direction 87. By the engagement of tabs 48, 50 within slots 52, 54, obturator barrel 14 is mounted within body 58 but is capable of relatively short axial movement for in proximal direction 87 only after safety arm 57 has been pivoted away from the safe position of FIG. 1 for the purposes to be discussed below. Obturator barrel 14 is biased in a distal direction 59 within obturator body 58 by an actuation force adjustment spring 60. Spring 60 is captured between an actuation force adjustment screw 62, housed within a threaded hole 64 formed in the proximal end 66 of body 58, and idler pulley support 20.

Cable 43 is moved, thus rotating blade 38, through the use of a cutting element driver 68. Driver 68 includes a cable clamp 70 which is clamped to cable 43 in the region adjacent a longitudinal slot 72 formed in obturator barrel 14. Cable clamp 70 is sized to fit within slot 72 and to move axially along the slot. Cable clamp 70 also includes a longitudinally extending slot or gap 74 which houses cable 43. Cable clamp 70 is secured to a generally tubular shuttle 76 which slides axially along obturator barrel 14. Shuttle 76 and cable clamp 70 each has a set of three aligned holes 78, 80 within which a set of screws 82 are mounted. Holes 78 in cable clamp 70 are threaded only in their ends farthest from holes 80; holes 80 and the remainder of holes 78 are through holes. Accordingly, tightening screws 82 cause cable clamp 72 squeezed tightly onto cable 43. Because of the engagement of cable clamp 70 within slot 72, the axial movement of cable clamp 70 and shuttle 76 is limited by the axial length of slot 72. Accordingly, the distance cable 43 can move is likewise so limited. Slot 72 is sized so that blade 38 makes one revolution when cable clamp 70 moves from one end of slot 72 to the other end.

The driving force behind cutting element driver 68 is provided by blade drive spring 84 which is captured between upper limit flange 44 and a radially extending flange 86 at the base of shuttle 76. Spring 84 thus normally biases shuttle 76 in distal direction 59. By moving shuttle 76 in a proximal direction 87, thus compressing spring 84 between flange 86 and upper limit flange 44, the unit can be armed. This armed condition is retained through the use of a pair of latching arms 88 pivotally mounted to shuttle 76 adjacent flange 86 by pins 90. In the armed or pre-use condition of FIGS. 1 and 3A, ledges 92 of latching arms 88 engage the proximal surface 94 of upper limit flange 44 thus keeping spring 84 compressed.

To permit actuation of blade 38, safety arm 57 is first moved in a clockwise direction from the safe position of FIG. 1 until arm 57 contacts a stop 93 formed on sidewall 56 of body 58. Doing so causes a projection or bump 97 on sidewall 56 to be removed from a second slot 99 formed in the inside surface of safety arm 57. The engagement of bump 97 within slot 99 helps to prevent the inadvertent movement of safety arm 57 from the safe position of FIG. 1. This movement of safety arm 57 permits tab 49 of upper limit flange 44 to move in slot 52 in proximal direction 87.

Latching arms 88 are released from upper limit flange 44 by the axial movement of obturator assembly 6 in proximal direction 87. This occurs when an inwardly extending release ring 95, extending inwardly from proximal end 66 of obturator body 58, engages angled camming surfaces 96 of latching arms 88 thus rotating arms 88 radially outwardly disengaging latching arms 88 from upper limit flange 44 thus permitting spring 84 to drive shuttle 76 and cable clamp 70 therewith in distal direction 59 along slot 72. This axial movement of cable clamp 70 causes similar movement of cable 43 causing blade 38 to rotate one revolution. As suggested in FIGS. 1 and 3B, blade 38 is safely housed within tip shells 34, 36 both when in the pre-use, armed condition of FIGS. 1 and 3B and after actuation, due to the appropriate sizing of slot 72.

Figure 2:
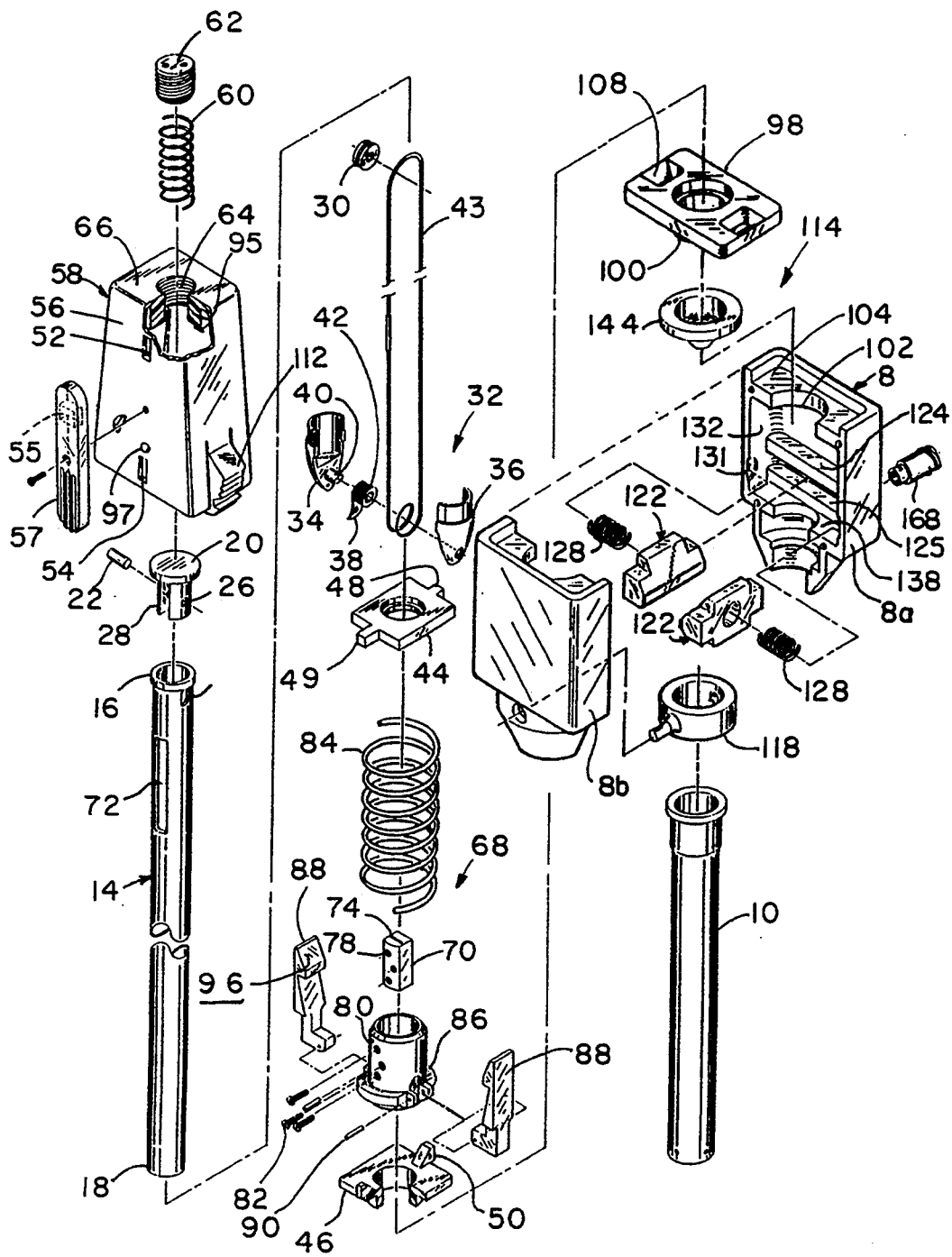
FIG. 2 is an exploded isometric view of the trocar of FIG. 1.
Figures 2A, 2B:
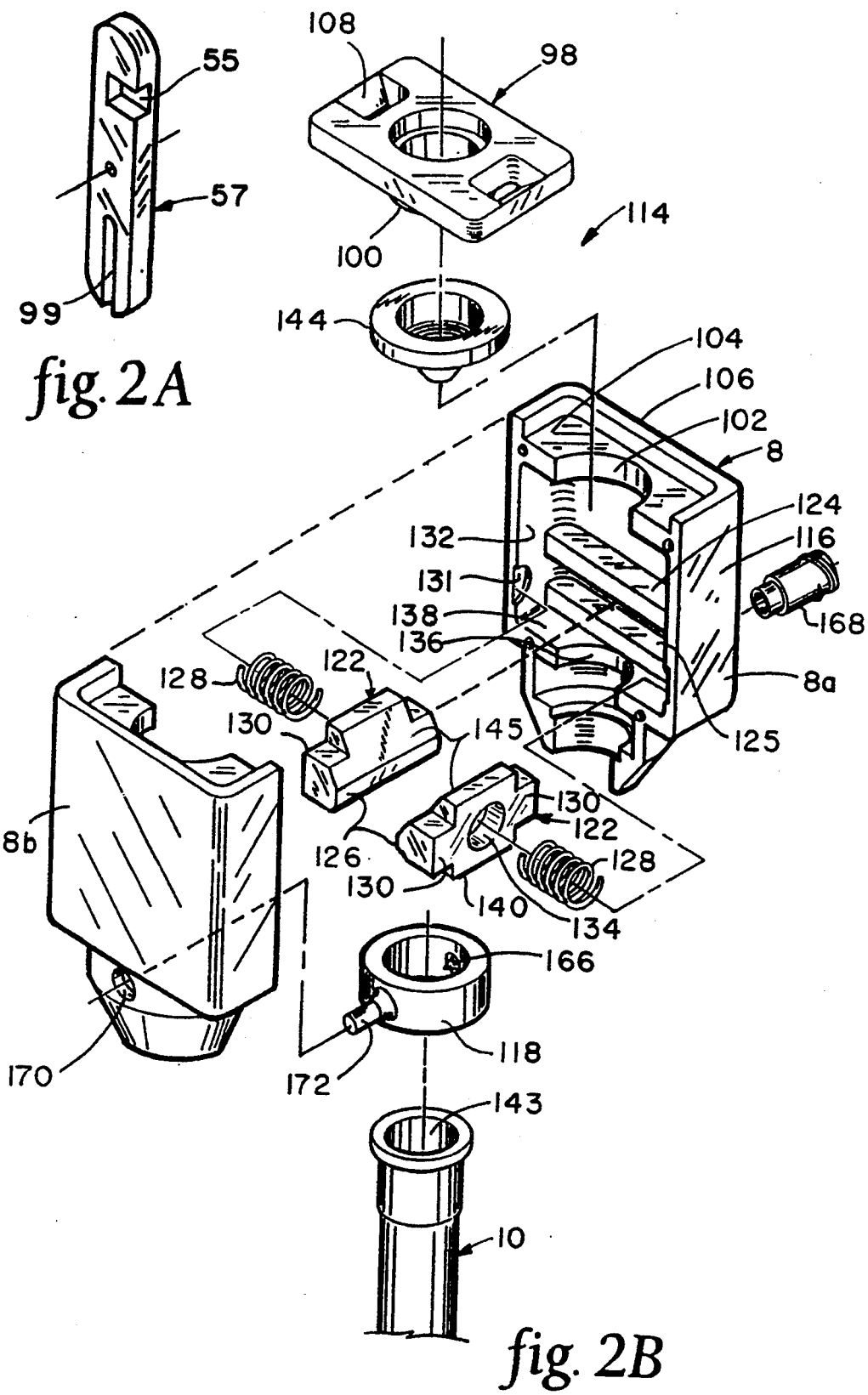
FIG. 2A is an enlarged isometric view of the inner surface of the safety arm of FIG. 2.
FIG. 2B is an enlarged exploded isometric view of the proximal end of the trocar body of FIG. 2.
Figure 3A:
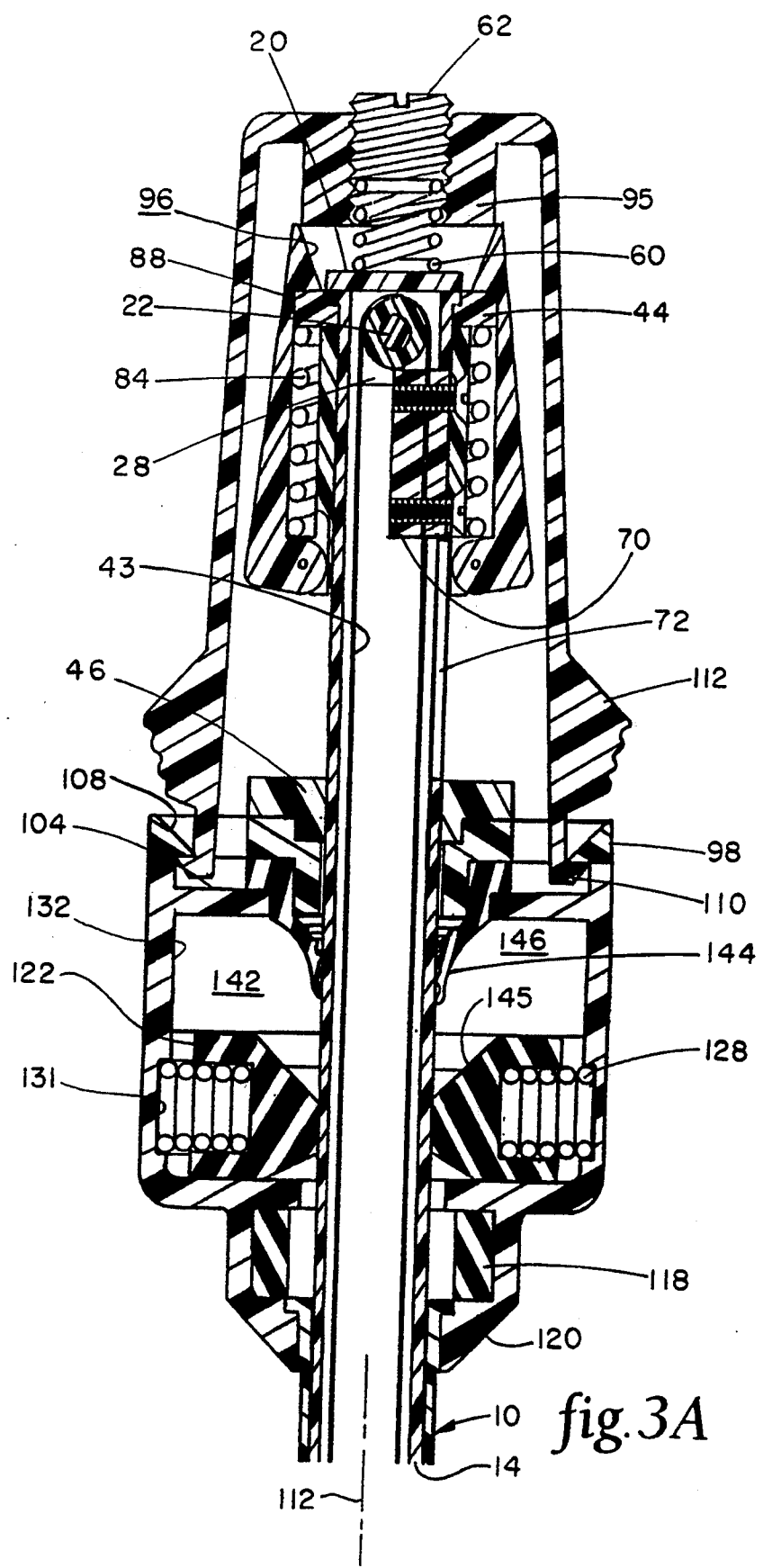
FIGS. 3A and 3B are cross-sectional views of proximal and distal portions of the trocar of FIG. 1.
Figure 3B:
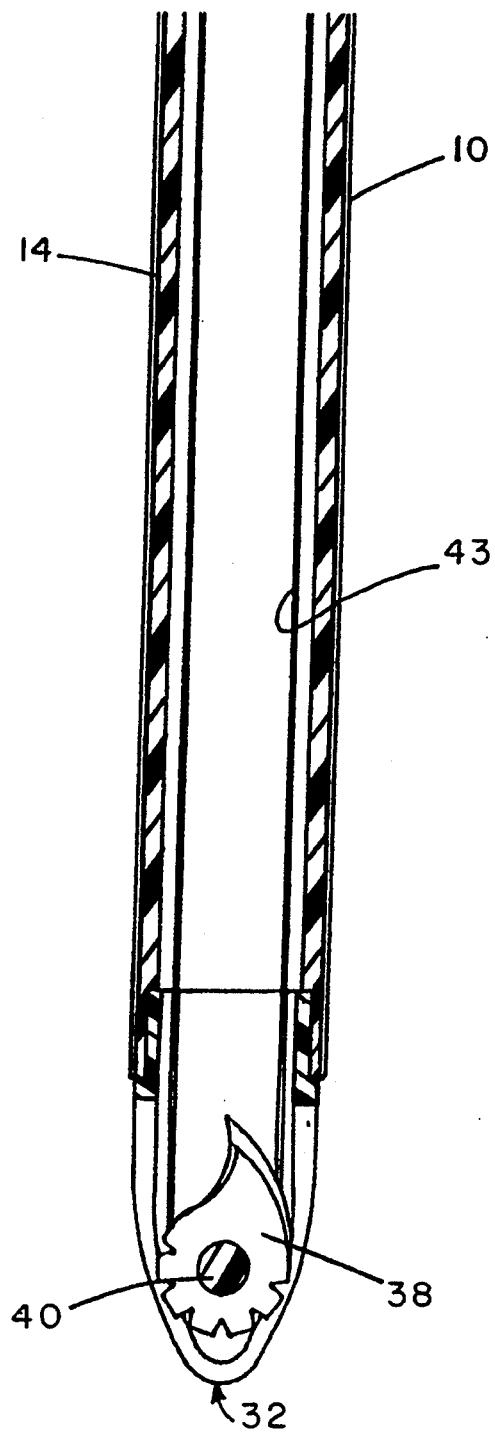
Figure 4:
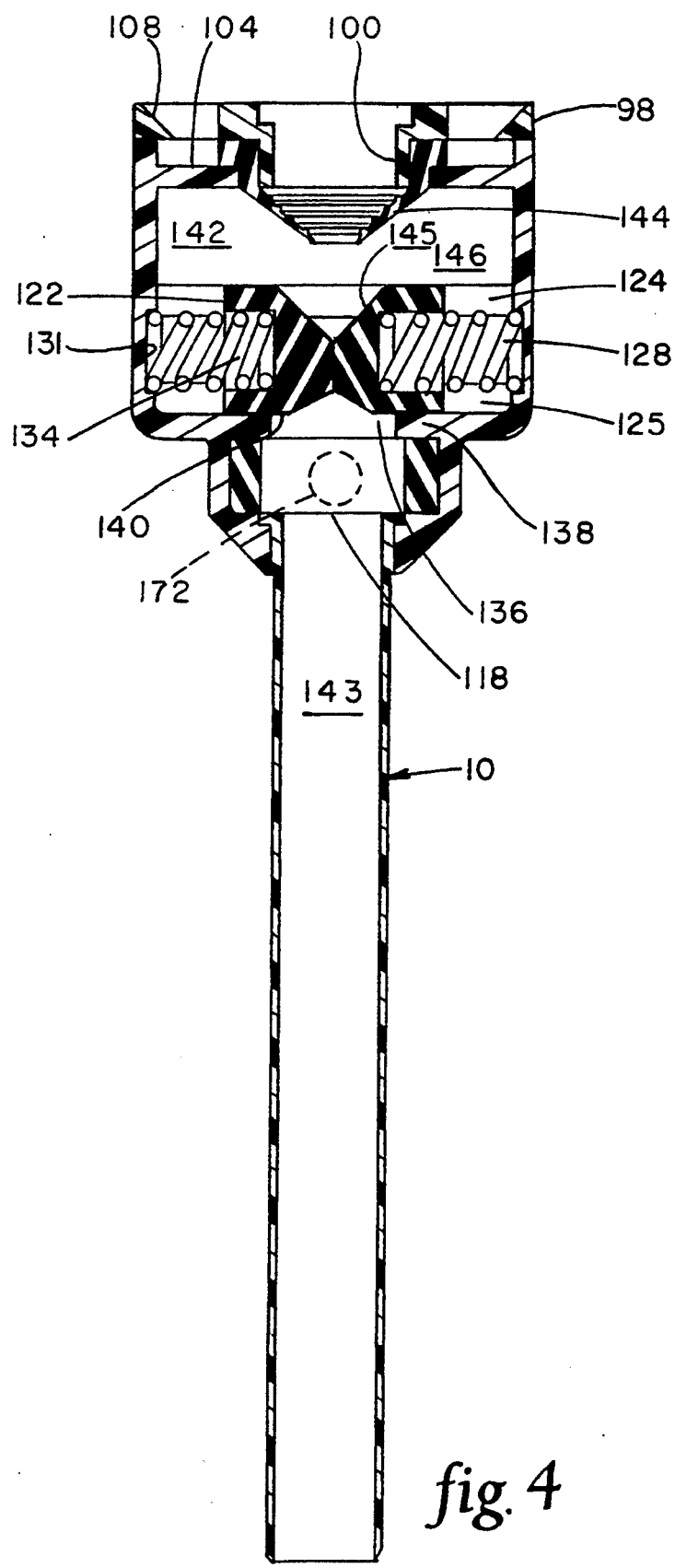
FIG. 4 is an enlarged cross-sectional view of the trocar body of FIGS. 1 and 2.

Trocar body 4, see FIGS. 2, 2B and 4, includes a locking plate 98 having a hollow cylindrical boss 100 sized to fit within a circular hole 102 formed in a bulkhead 104 at the proximal end 106 of trocar base 8. Locking plate 98 is secured to proximal end 106 by an adhesive. Locking plate 98 has a pair of tapered latching surfaces 108 positioned and sized to accommodate the distal ends 110 of resilient docking hooks 112 at the distal end of obturator body 58. Placing the distal end of obturator body 58 against locking plate 98, shown in FIGS. 1 and 3A, causes docking hooks 112 to engage latching surfaces 108, to be biased inwardly and then to snap outwardly to latch beneath surfaces 108 thus securing obturator assembly 6 to trocar body 4.

Trocar body 4 includes a sealing assembly 114 mounted within the proximal, enlarged rectangular portion 116 of trocar base 8, and an elastomeric vent ring 118 positioned adjacent an inwardly and distally tapering region 120 at the distal end of trocar base 8. Sealing assembly 114 includes a pair of elastomeric sealing elements 122 having generally T-cross-sectional shapes. Sealing elements 122 are slidably mounted between the halves 8a, 8b of trocar base 8 and between guide plates 124, 125. Guide plates 124, 125 extend within halves 8a, 8b of trocar base 8 along an inner sidewall 132 of base 8. Sealing elements 122 have wing extensions 130 which fit between guide plates 124, 125. Sealing elements 122 are made of blocks of elastomeric material, such as 50 Durometer silicone rubber, and have elastomeric confronting sealing surfaces 126 covered with 35 Durometer silicone rubber. Sealing elements 122 are biased by springs 128 between an object passing position of FIG. 3A and a sealing position of FIG. 4. One end of each spring 128 is mounted within a recess 131 formed in inner sidewalls 132 of sides 8a, 8b of trocar base 8 while the other end of each spring 128 is housed within holes 134 formed in sealing elements 122. Springs 128 bias sealing elements 122 to the sealing position of FIG. 4.

Trocar body 8 includes a lower opening 136 formed in a lower bulkhead 138. Sealing elements 122 include distal sealing surfaces 140 which lie against the proximal surface of bulkhead 138. When sealing elements 122 are in the sealing position of FIG. 4, surfaces 140 cover opening 136 and sealing surfaces 126, which extend from inner sidewall 132 of half 8a to inner sidewall 132 of half 8b, are in sealing contact, thus sealing the proximal portion 142 of interior 146 of trocar body 8 from the interior 143 of trocar barrel 10.

Sealing elements 122 both have proximal surfaces 145. The proximal surfaces 145 taper or extend radially inwardly and axially distally. This angular orientation of surfaces 145, when sealing elements 122 are in the sealing position of FIG. 4, permits an obturator assemble 6 to force each sealing element 122 laterally along a linear path by simply pressing on surfaces 145 with tip assembly 32.

Conical sealing assembly 114 includes an object seal in the form of a conical sealing element 144 used to form a fluid seal between the interior 146 of base 8 and the object, such as obturator barrel 14, passing therethrough. Conical sealing element 144 includes an outer flange 148 surrounding a main cylindrical portion 150 and, continuing in distal direction 59, an inwardly and distally directed conical portion 152. Conical portion 152 has an inner conical surface 154 defining an included angle of about 90° in the preferred embodiment. Conical portion 152 has an outer conical surface 156 defining an included angle of about 106° so that conical portion 152 has a mean included angle of about 98° and a wall taper of about 8°. Element 144 is housed within body 8 and is captured between cylindrical boss 100 of locking plate 98 and hole 102. Conical sealing element 144 is preferably made from 50 Durometer silicone rubber for its toughness and good sealing qualities.

Conical portion 152 has an opening 158 at a distal end thereof sized to be somewhat smaller than the smallest diameter object, typically an obturator or surgical instrument, expected to pass therethrough. In the preferred embodiment this diameter is approximately 4.6 mm. The inside diameter of cylindrical portion 150 is about 15 mm. It has been found that the particular configuration of conical portion 152 of conical sealing element 144 provides a good gas seal over a range of sizes of objects used within trocar body 4. Since the inside diameter of cylindrical portion 150 is about 15 mm, the range of diameters of objects which can be used with this embodiment of the invention can be as great as about 3:1.

Figure 5:
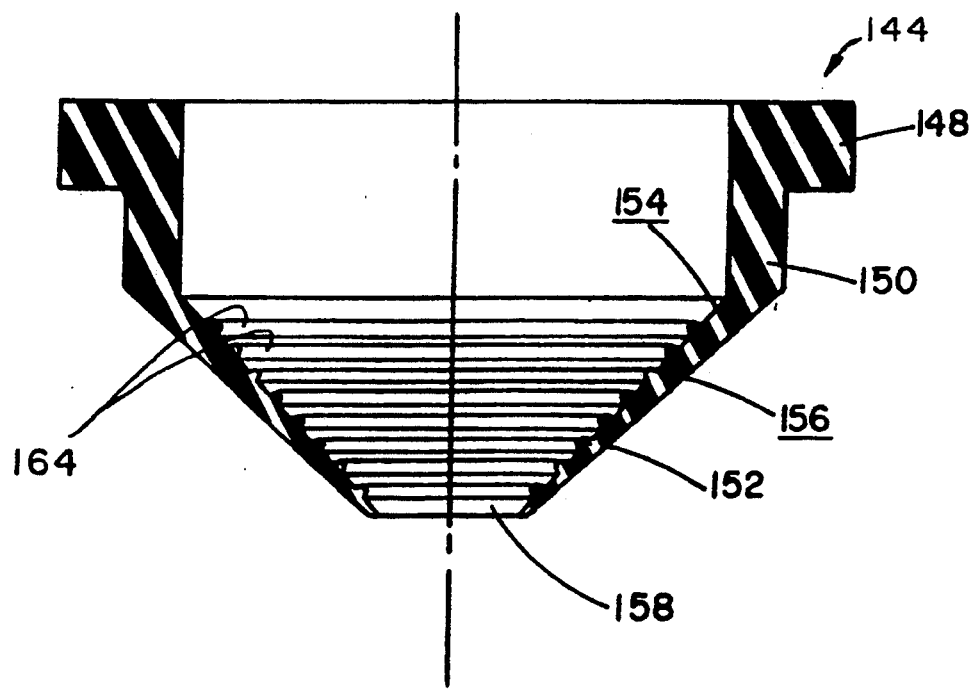
FIG. 5 is a cross-sectional view of the conical sealing element in its unstressed state of FIG. 4.

As can be seen in FIG. 5, inner surface 154 has a series of raised ring-like ridges 164 formed thereon. Ridges 164 are used to reduce sliding friction of tubes passing through conical sealing element 144. In the preferred embodiment, 8 generally evenly spaced rings, each about 0.5 mm high, are used. If desired, surface 154 can be made with a low-friction surface material or a biocompatible lubricant to reduce sliding friction and thus minimize loss of sensitivity to the physician when manipulating the instrument.

Figure 6A:
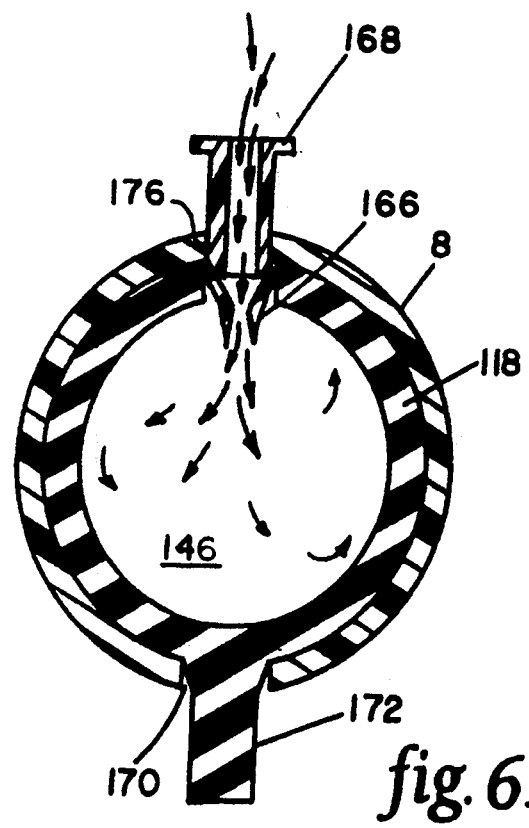
FIGS. 6A and 6B are plan cross-sectional views of the trocar body and elastomeric vent ring of FIG. 4 shown with pressurized fluid passing into the interior of the trocar body in FIG. 6A and the opening of a vent path to the ambient environment in FIG. 6B.
Figure 6B:
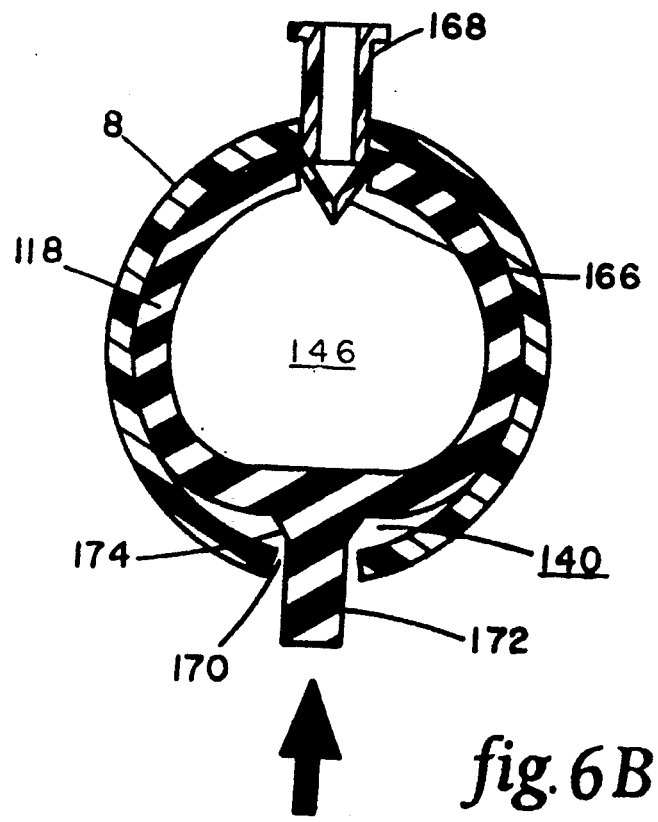

Vent ring 118, see FIGS. 6A and 6B, is made from an elastomeric material, such as 50 Durometer silicone rubber, and includes an integral conical check valve 166 which is aligned with a radially extending Luer lock fitting 168 mounted within a hole 176 in base 8. A remote pressure source (not shown) is connected to fitting 168. Check valve 166 allows fluid to pass into interior 146 of body 8, as suggested in FIG. 6A, but not the reverse, as suggested in FIG. 6B. Base 8 has a radially extending bore 170 through which a radial extension 172 of ring 118 passes. The enlarged base 174 of extension 172 is biased against bore 170 with sufficient force to normally seal bore 170. To vent interior 146, the user simply presses on extension 172 which deflects ring 118 radially inwardly as shown in FIG. 6B. This provides a vent path from interior 146 to the ambient environment through bore 170. Accordingly, with the invention separate medical devices need not be used to either pressurize or vent the body cavity accessed by trocar 2.

The present invention is made from conventional biocompatible materials. For example, blade 38, springs 60, 84, 128, cable 43 plus the various pins and screws are preferably made from stainless steel. Conical element 144, sealing elements 122, sealing surfaces 126 and vent ring 118 are preferably made of suitable elastomeric materials, as discussed above. The remaining parts can be made of polycarbonate or other appropriate materials. It is particularly important that trocar base 8 and trocar barrel 10 be made of biocompatible materials.

In use, the physician first makes a small incision with a scalpel at the point of entry. The tapered tip of trocar 2 is then pressed through the slit in the patient's skin, through the fatty tissue layer until the tip reaches the muscular fascial layer. At this point safety arm 57 is pivoted to expose slot 52 so that further force on trocar 2 causes obturator assembly 6 to move proximally causing latching arms 88 to be pivoted outwardly to permit cable clamp 70 to be driven distally by spring 84 thus rotating blade 38 one revolution and making a linear incision through the patient's fascial layer. With blade 38 safely stowed back between tip shells 34, 36, the physician continues to force obturator assembly 10 through the newly created incision in the fascial layer so to properly position trocar barrel 10 within the body cavity of the patient.

Obturator assembly 6 is then removed from trocar body 4 by pressing on docking hooks 112 and lifting the obturator assembly in proximal direction 87. As the tip of obturator assembly 6 passes sealing elements 122, the sealing elements return to their sealing positions of FIG. 4 to prevent escape of fluid pressure through trocar 2. As the tip of obturator assembly 6 passes through conical sealing element 144, the conical element returns to its open, unflexed condition of FIGS. 4 and 5.

An endoscopic surgical instrument, such as an endoscope, can then be inserted through trocar body, past sealing assembly 114, through the interior 186 of trocar barrel 10 and into the body cavity. The surgical instrument is surrounded by surface 154 of conical element 144 to help prevent the loss of pressurization within the body cavity. The body cavity can be pressurized by simply mounting a pressurized line to fitting 168 and supplying pressurized fluid, typically $CO_2$, into interior 146, through interior 143 and into the body cavity. The pressure in the body cavity can be reduced by pressing on extension 172 which deflects vent ring 118 and permits fluid flow through bore 170 and to the ambient environment.

Modifications and variations can be made to the disclosed embodiment without departing from the subject of the invention as defined in the following claims. For example, sealing assembly 114 could be used with other obturators, such as conventional 3-bladed obturators or either of the obturators disclosed in the above-mentioned applications entitled TROCAR WITH IMPROVED OBTURATOR and TROCAR WITH PIVOTAL SAFETY SHIELD. Also, sealing assembly 114 could be used with other medical devices designed for minimally invasive surgical procedures. The proximal/distal relationship of sealing elements 122 and conical sealing element 144 could be reversed. Sealing surfaces 126 need not be straight. Sealing elements 122 could be biased towards one another other than by using mechanical springs, such as by magnetic force or by pneumatic springs. Also, sealing elements 122 may move along linear lateral paths which are not totally radial but have an axial component as well.

What is claimed is:

1. A medical device, designed for minimally invasive surgical procedures, comprising:
    a body having proximal and distal ends and a hollow interior defining a path between the proximal and distal ends;
    an object sized to pass along the path; and
    a seal mounted within the body and fluidly sealing the path with and without the object directed along the path and into the hollow interior, the seal including:
    first and second sealing elements positioned along the path, each sealing element movable laterally along a linear path from a sealing position to an object passing position;
    means for biasing the sealing elements towards the sealing position;
    said first and second sealing elements having confronting sealing surfaces which sealingly engage one another when the sealing elements are in the sealing position so to seal the path when an object is not positioned along the path, said sealing elements configured to permit the object to pass therethrough; and
    an object seal, positioned along the path, configured to sealably engage the object when the object is directed along the path to provide a fluid seal between the object and the hollow interior.

2. The medical device or claim 1 wherein the object seal includes a flexible, elastic, conical element, positioned along the path, tapering inwardly from a first end in a direction from the proximal end of the body towards the distal end of the body, the conical element including a central opening at a second end thereof, the central opening, when the conical element is in a relaxed, contracted position, having a diameter which is at least slightly smaller than the diameter of the object to provide a fluid seal between the object and the hollow interior being movable from the relaxed, contracted position to an open position so that the conical element is adapted to engage objects having an outside diameter of x to at least 2x.

3. The medical device of claim 2 wherein the conical element has an inner surface and the inner surface has a series of raised elements thereon.

4. The medical device of claim 1 wherein the object is an obturator.

5. The medical device of claim 1 wherein the medical device is a trocar.

6. The medical device of claim 1 wherein the sealing elements are each made of a block of an elastomeric material.

7. The medical device of claim 1 wherein the biasing means include spring means for biasing the sealing elements towards the sealing position.

8. The medical device of claim 1 wherein the sealing surfaces are elastomeric sealing surfaces.

9. The medical device of claim 8 wherein the sealing elements each include an elastomeric body to which the elastomeric sealing surfaces are secured.

10. The medical device of claim 1 wherein the sealing elements each includes a proximal surface tapering radially inwardly towards the distal end of the body when the sealing elements are in the sealing position.

11. The medical device of claim 1 wherein the sealing surfaces are straight.

12. The medical device of claim 1 further comprising:
a resilient vent ring, having an interior surface and an exterior surface, mounted along the path within the hollow interior of the body between the object seal and the distal end of the body;
a passageway formed from the interior surface, through the body and to a port exterior of the body;
a check valve positioned along the passageway to permit fluid flow through the port, along the passageway and into the hollow interior but to prevent fluid flow from the hollow interior, through the passageway and through the port; and
a vent ring deflector extending from the vent ring through a vent in the body to a user-accessible position exterior of the body, the vent ring deflector movable from a normally sealed position, at which the vent ring and vent ring deflector seal the vent to prevent fluid flow from the hollow interior and through the vent, to a vent position, at which the vent ring is deflected inwardly into the hollow interior to permit fluid flow from the hollow interior, through the vent and into a region exterior of the body.

13. The medical device of claim 12 wherein the vent ring is made of an elastomeric material.

14. The medical device of claim 12 wherein the check valve is a one-piece element with the vent ring.

15. The medical device of claim 12 wherein the port is part of a Luer lock fitting.

16. The medical device of claim 12 wherein the vent ring deflector extends radially from the vent ring and is a one-piece extension of the vent ring.

17. A trocar comprising:
a body having proximal and distal ends and a hollow interior defining a path between the proximal and distal ends;
an object sized to pass along the path; and
a seal mounted within the body and fluidly sealing the path with and without the object directed along the path and into the hollow interior, the seal including:
first and second sealing elements positioned along the path, each sealing element movable radially along a linear path from a sealing position to an object passing position;
means for biasing the sealing elements towards the sealing position;
said first and second sealing elements having confronting sealing surfaces which sealingly engage one another when the sealing elements are in the sealing position so to seal the path when an object is not positioned along the path, said sealing elements configured to permit the object to pass therethrough;
a flexible, elastic, conical element, positioned along the path, tapering inwardly from a first end in a direction from the proximal end of the body towards the distal end of the body, the conical element including a central opening at a second end thereof, the central opening, when the conical element is in a relaxed, contracted position, having a diameter which is at least slightly smaller than the diameter of the object to provide a fluid seal between the object and the hollow interior;
the conical element having an inner surface and the inner surface having a series of raised ring-like elements thereon; and
the conical element being movable from the relaxed, contracted position to an open position so that the conical element is adapted to engage objects having an outside diameter of x to at least 2x.

18. A seal for use with a surgical object and hollow body defining a path, the surgical object and the body being used in a minimally invasive surgical procedure, the body having proximal and distal ends, comprising:
first and second sealing elements positioned along the path, each sealing element movable laterally along a linear path from a sealing position to an object passing position;
first and second spring biasing the sealing elements towards the sealing position;
said first and second sealing elements having confronting sealing surfaces which sealingly engage one another when the sealing elements are in the sealing position so to seal the path when an object is not positioned along the path, said sealing elements configured to permit the object to pass therethrough.

19. The seal of claim 18 wherein the sealing elements are each made of a block of elastomeric material.

20. The seal of claim 18 wherein the sealing surfaces are elastomeric sealing surfaces.

21. The seal of claim 18 wherein the sealing elements each includes an elastomeric body to which the elastomeric sealing surfaces are secured.

22. The seal of claim 18 wherein the sealing elements each includes a proximal surface tapering radially inwardly towards the distal end of the body when the sealing elements are in the sealing position.

23. The seal of claim 18 wherein the sealing surfaces are straight.

24. The seal of claim 18 further comprising an object seal, positioned along the path, configured to sealably engage the object when the object is directed along the path to provide a fluid seal between the object and the hollow interior.

25. The seal of claim 24 wherein the object seal includes:

a flexible, elastic, conical element, positioned along the path, tapering inwardly from a first end in a direction from the proximal end of the body towards the distal end of the body, the conical element including a central opening at a second end thereof, the central opening, when the conical element is in a relaxed, contracted state, having a diameter which is at least slightly smaller than the diameter of the object to provide a fluid seal between the object and the hollow body.

26. The seal of claim 25 wherein the conical element has an inner surface and the inner surface has a series of raised ring-like elements thereon.

27. The seal of claim 25 wherein the conical element is adapted to engage surgical objects having outside diameter of x to at least 2x.

28. A medical device designed for minimally invasive surgical procedures comprising:

a body having proximal and distal ends and a hollow interior defining a path between the proximal and distal ends;

an object sized to pass along the path;

a seal mounted within the body and fluidly sealing the path with and without the object directed along the path and into the hollow interior, the seal including:

first and second sealing elements positioned along the path, each sealing element movable laterally along a linear path from the sealing position to an object passing position;

means for biasing the sealing elements towards the sealing position;

said first and second sealing elements having confronting sealing surfaces which sealingly engage one another when the sealing elements are in the sealing position so to seal the path when an object is not positioned along the path, said sealing elements configured to permit the object to pass therethrough; and a resilient vent ring, having an interior surface and an exterior surface, mounted along the path within the hollow interior of the body between the seal and the distal end of the body, the vent ring adapted to permit fluid flow from the exterior of the body into the hollow interior, but to prevent fluid flow from the hollow interior to the exterior of the body.

* * * * *